US00PP17282P2

(12) United States Plant Patent
Bradford

(10) Patent No.: US PP17,282 P2
(45) Date of Patent: Dec. 19, 2006

(54) PEACH TREE NAMED 'IVORY DUCHESS'

(50) Latin Name: *Prunus persica*
Varietal Denomination: IVORY DUCHESS

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 58 days.

(21) Appl. No.: 11/311,171

(22) Filed: Dec. 20, 2005

(51) Int. Cl.
*A01H 5/00* (2006.01)

(52) U.S. Cl. ..... Plt./195
(58) Field of Classification Search ..... Plt./195
See application file for complete search history.

(56) References Cited
U.S. PATENT DOCUMENTS

PP11,205 P 2/2000 Bradford

*Primary Examiner*—Kent Bell
*Assistant Examiner*—Annette H Para

(57) ABSTRACT

The present invention relates to a peach tree, *Prunus persica*, and more particularly to a new and distinct variety characterized by a large size, vigorous, hardy, self-fertile, productive and regular bearing tree. The fruit matures under the ecological conditions described in late May, with first picking on May 28, 2005. The fruit is large in size, sweet and sub-acidic in flavor, globose with some tipping on the apex in shape, clingstone in type, white in flesh color, mostly red in skin color, and firm in texture. The variety was developed as a first generation cross using an unnamed white flesh nectarine (unpatented) as the selected seed parent and an unnamed yellow flesh peach (unpatented) as the selected pollen parent.

1 Drawing Sheet

Botanical classification: *Prunus persica.*
Variety denomination: 'IVORY DUCHESS'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'IVORY DUCHESS'. The present variety was hybridized by me in 2001, grown as a seedling on its own root in my greenhouse, and transplanted to a cultivated area of my experimental orchard at Bradford Farms near Le Grand, Calif. in Merced County (San Joaquin Valley).

The variety was developed as a first generation cross using an unnamed white flesh nectarine (unpatented) as the selected seed parent and an unnamed yellow flesh peach (unpatented) as the selected pollen parent. The unnamed seed parent was a first generation cross of 'Spring Bright' (U.S. Plant Pat. No. 7,507) nectarine by an unnamed white flesh nectarine (unpatented). The unnamed pollen parent was a first generation cross of 'Spring Bright' (U.S. Plant Pat. No. 7,507) nectarine by an unnamed yellow peach (unpatented). A single tree from the stated cross was selected as the claimed variety. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is substantially distinguished from its common seed and pollen grandparent, 'Spring Bright' (U.S. Plant Pat. No. 7,507) nectarine, by producing white flesh peaches instead of yellow flesh nectarines and by maturing about one month earlier.

The present variety is most similar to 'Ivory Princess' (U.S. Plant Pat. No. 11,205) peach, by producing fruit that is clingstone in type, white in flesh color, mostly red is skin color, firm in texture, and sub-acid in flavor, but is distinguished therefrom by requiring less chilling hours, by blooming earlier, and by producing fruit that matures about eight days earlier.

SUMMARY OF VARIETY

In summary, the present variety is characterized by a large size, vigorous, hardy, self-fertile, productive and regular bearing tree. The fruit matures under the ecological conditions described in late May, with first picking on May 28, 2005. The fruit is large in size, sweet and sub-acidic in flavor, globose with some tipping on the apex in shape, clingstone in type, white in flesh color, mostly red in skin color, and firm in texture.

DRAWING

The accompanying photograph exhibits four whole fruits positioned to display the characteristics of the skin and form, one fruit divided transversely to the suture plane to reveal the flesh and stone, a representative stone, a typical tip shoot, and two insets depicting buds and blossoms.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 1, 2005, on the original tree during its fourth growing season. All major color code designations are by reference to the Inter-Society Color Council, National Bureau of Standards. Common color names are also used occasionally.

Tree

Size: Medium, reaching a height of 9' [2.7 m.] and a spread of 9' [2.7 m.] after four growing seasons utilizing typical dormant pruning.

Vigor: Vigorous, responding typically to irrigation and fertilization. The variety grows about 3' [0.9 m.] of surplus top-growth during the spring and summer. The plant should be grown on a standard commercial rootstock for production purposes.

Growth: Spreading and dense.

Form: Trained to be vase formed by pruning.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 400 hours.

Trunk:

*Size.*—Medium, with a maximum diameter of 3½" [89 mm.] after the fourth growing season.

*Texture.*—Shaggy.

*Bark color.*—A Grayish brown [61. gy.Br] and Deep brown [56. deep Br] variegation.

*Lenticels.*—Approximate Number Per Square Inch: 12. Color: Light yellowish brown [76. 1 .yBr]. Average Size: ⅛" [3.2 mm.] to ⅜" [9.5 mm.]. Shape: Eye-shaped to elongated.

Branches:

*Size*—Diameter of limb is 1¾" [44.5 mm.] measured 12" above the crotch and 1⅜" [34.9 mm.] measured 12" above the first fork.

*Texture.*—Smooth, increasing roughness with age.

*Color.*—1st Year Wood Topside: Light grayish red [18. 1 .gy.R]. 1st Year Wood Underside: Brilliant yellow green [116. brill.YG]. Older Wood: Moderate brown [58. m.Br].

*Lenticels.*—Approximate Number Per Square Inch: 50. Color: Light yellowish brown [76. 1 .yBr]. Typical size: 1/64" [0.4 mm.] to ⅛" [3.2 mm.]. Shape: Eye-shaped to elongated.

Leaves:

*Size.*—Medium. Average length: 5⅞" [149.2 mm.]. Average width: 1 9/16" [39.7 mm.].

*Arrangement.*—Alternate.

*Thickness.*—Medium.

*Form.*—Elliptical.

*Apex.*—Acuminate.

*Base.*—Rounded.

*Surface*—Smooth.

*Color.*—Dorsal Surface: Dark yellowish green [137. d.yG]. Ventral Surface: Moderate yellowish green [136. m.yG].

*Margin.*—Finely serrate.

*Venation.*—Pinnately net veined.

*Petiole.*—Average length: ⅜" [9.5 mm.]. Average thickness: 1/16" [1.6 mm.]. Color: Strong yellow green [117. s.YG].

*Stipules.*—Number: 2 to 6 per growing tip. Average Length: 5/16" [7.9 mm.]. Color: Light yellow green [119. 1 .YG] toward the tip, Moderate Red [15. m.R] toward the base.

*Glands.*—Number: Usually 2 to 4. Position: Positioned alternately on petiole and base of blade. Size: Small. Form: Globose. Color: Light yellow green [119. 1 . YG] when young acquiring Moderate brown [58. m.Br] centers with age.

*Leaf buds.*—Medium, pointed.

Flower buds:

*Hardiness.*—Hardy, with respect to central California winters.

*Diameter.*—Typically ⅜" [9.5 mm.] 1 week before bloom.

*Length.*—Typically ½" [12.7 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepals and petal locations alternately positioned.

*Type.*—Showy, large.

*Average flower diameter.*—1⅞" [47.6 mm.].

*Number of petals.*—Usually five, with extra petal fragments common, a few double blossoms.

*Petal shape.*—Circular to oval.

*Petal margin.*—Somewhat wavy, especially toward the base.

*Average petal diameter.*—¾" [19.1 mm.].

*Average petal length.*—13/16" [20.6 mm.].

*Petal apex.*—Rounded.

*Petal base.*—Irregularly rounded.

*Petal color.*—Pale pink [7. p.Pk] toward the apex, Light purplish pink [249. 1 . pPk] toward the base.

*Anther color.*—Dark red [16. d.R] over Pale yellow [89. p.Y] centers at bloom onset.

*Stigma color.*—Brilliant greenish yellow [98. brill.gY].

*Sepal color.*—Dark purplish red [259. d.pR].

*Sepal length.*—5/16" [8 mm.].

*Sepal width.*—¼" [6 mm.].

*Average pistil length.*—11/16" [17.5 mm.].

*Average stamen length.*—⅝" [15.9 mm.].

*Fragrance.*—Moderate.

*Blooming period.*—Early compared to other varieties.

*Onset of bloom.*—One percent on Feb. 11, 2005.

*Date of full bloom.*—Feb. 19, 2005.

*Duration of bloom.*—One to two weeks, dependent on ambient temperature.

*Number per cluster.*—1 to 3 with single flowers most common.

FRUIT

Maturity when described: Firm ripe, Jun. 1, 2005.

Date of first picking: May 28, 2005, compared to a starting date of Jun. 5, 2005, for 'Ivory Princess'.

Date of last picking: Jun. 7, 2005.

Size: Uniform, large.

*Average diameter axially.*—3 1/16" [77.8 mm.].

*Average diameter across cheek plane.*—3" [76.2 mm.].

*Average diameter across suture plane.*—3" [76.2 mm.].

*Typical weight.*—8.1 ounces [230 grams].

Form: Uniform, symmetrical. Longitudinal Section Form — Round to slightly oval. Transverse Section Through Diameter — Round.

Suture: A shallow groove extending from the base to slightly beyond the apex, sharper toward the stem cavity and apex, rounded along the side, depressions around the pistil point.
Ventral surface: Rounded, slightly lipped toward apex.
Lips: Usually equal near the apex, slightly unequal along side.
Cavity: Large, flaring, elongated in the suture plane, suture showing on one side, Pale yellow [89. 1 .Y] stem markings typical.
*Depth.*—⅝" [15.9 mm.].
*Breadth.*—1 3/16" [30.2 mm.].
Base: Rounded to somewhat truncate.
Apex: Rounded.
Pistil point: Apical, somewhat mammiform.
Stem: Medium.
*Average length.*—⅜" [9.5 mm.].
*Average width.*—3/16" [4.8 mm.].
Skin:
*Thickness.*—Medium, tough.
*Surface.*—Medium.
*Tenacity.*—Tenacious to flesh.
*Astringency.*—Nonastringent.
*Tendency to crack.*—Slight in wet season.
*Color.*—Very deep red [14. v.deep R] mottled over a Dark pink [6. d.Pk] background with Pale yellow green [121. p.YG] areas where sun protected.
Down: Scant, short in length, does not roll up when rubbed.
Flesh:
*Color.*—Greenish white [153. gWhite] with very slight Moderate pint [5. m.Pk] flecking near the skin.
*Surface of pit cavity.*—Clingstone with Pale yellow green [121. p.YG] broken fibers when twisted away from the stone.
*Amygdalin.*—Scarce.
*Juice.*—Abundant, rich.
*Texture.*—Firm, crisp and melting.
*Fibers.*—Abundant, fine and tender.
*Ripens.*—Slightly earliest at the apex and along the lips.
*Flavor.*—Mildly sub-acidic with an average 14 brix.
*Aroma.*—Very slight.
*Eating quality.*—Very good.

STONE

Type: Clingstone.
Form: Oval.
Hilum: Narrow, oblong.
Base: Straight, rounded.
Apex: Rounded with a sharp tip at apex.
Sides: Equal.
Surface: Irregularly furrowed very close to the apex, vertical grooves on both sides of the dorsal fin, a single groove along ventral edge, and strongly pitted toward base to center.
Ridges: Jagged.
External color: Light yellowish brown [76. 1 . yBr].
Internal color when cracked: Pale orange yellow [73. p.OY].
Cavity surface color: Light orange yellow [70. 1 .OY].
Average pit wall thickness: ¼" [6.4 mm.].
Average width: 1" [25.4 mm.].
Average length: 1 7/16" [36.5 mm.].
Average breadth: 11/16" [17.5 mm.].
Tendency to split: Moderate in wet season.
Kernel:
*Form.*—Oval.
*Pellicle color.*—Grayish yellowish brown [80. gy.yBr].
*Skin color.*—Pale yellow [89. p.Y] when first removed.
*Vein color.*—Stong yellowish brown [74. s.yBr].
*Taste.*—Very bitter.
*Viable.*—Only by using embryoculture techniques.
*Average width.*—15/32" [11.9 mm.].
*Average length.*—¾" [19.1 mm.].
*Amygdalin.*—Abundant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual suceptibilities noted.

Other Notes

Altough the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Ivory Princess' (U.S. Plant Pat. No. 11,205) peach, by producing fruit that is clingstone in type, white in flesh color, mostly red is skin color, firm in texture, and sub-acid in flavor, but is distinguished therefrom by requiring much less chilling hours, by blooming earlier, and by producing fruit that matures about eight days earlier.

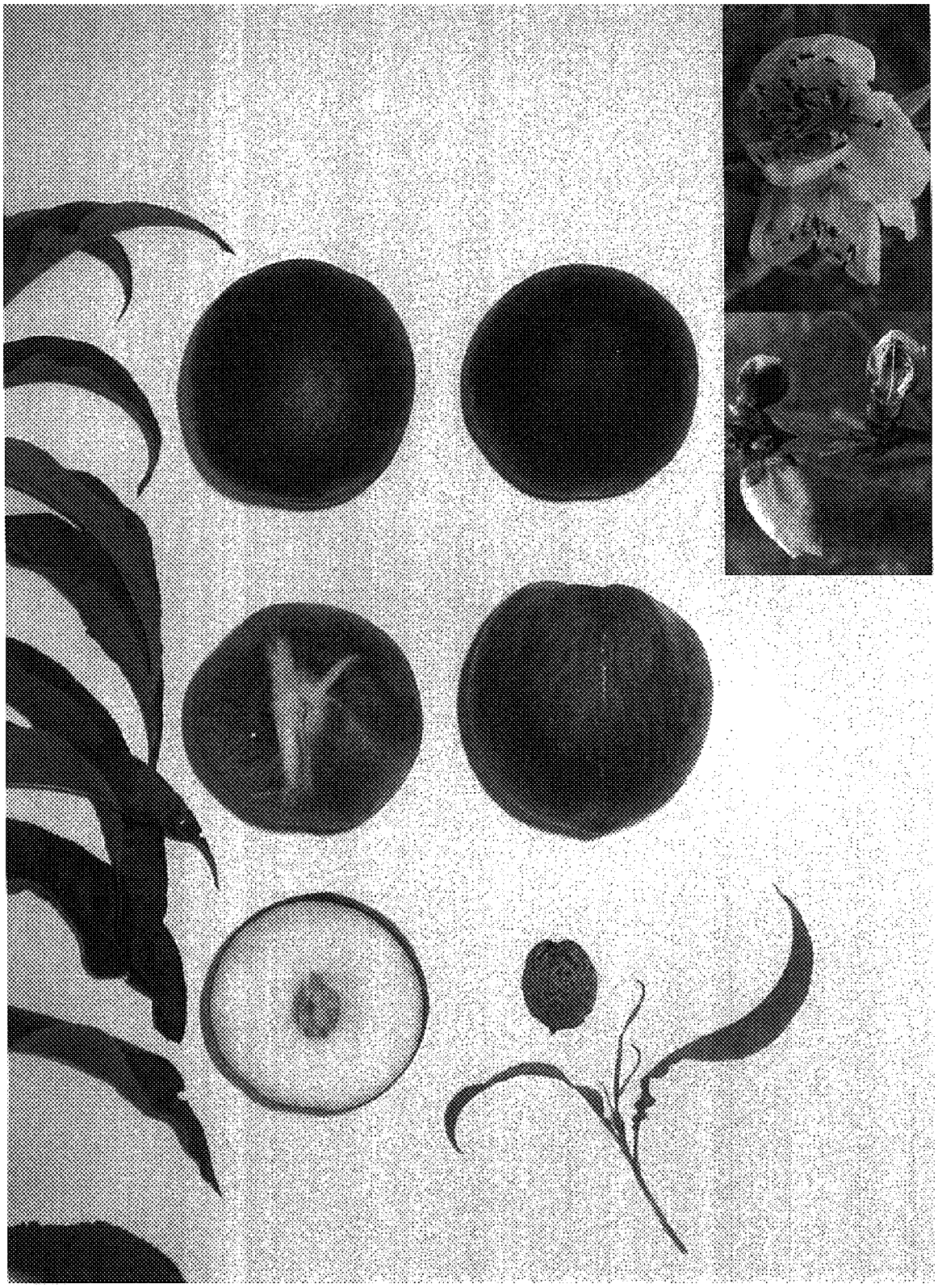

* * * * *